US009938574B2

(12) United States Patent
Fontana et al.

(10) Patent No.: US 9,938,574 B2
(45) Date of Patent: Apr. 10, 2018

(54) METHOD AND KIT FOR DETECTING A WILD-TYPE AND/OR A MUTATED TARGET DNA SEQUENCE

(71) Applicant: Menarini Silicon Biosystems S.p.A., Bologna (IT)

(72) Inventors: Francesca Fontana, Bologna (IT); Nicolo Manaresi, Bologna (IT)

(73) Assignee: Menarini Silicon Biosystems, S.p.A., Bologna (IT)

( * ) Notice: Subject to any disclaimer, the term of this patent is extended or adjusted under 35 U.S.C. 154(b) by 356 days.

(21) Appl. No.: 14/439,859

(22) PCT Filed: Oct. 31, 2013

(86) PCT No.: PCT/IB2013/059827
§ 371 (c)(1),
(2) Date: Apr. 30, 2015

(87) PCT Pub. No.: WO2014/068519
PCT Pub. Date: May 8, 2014

(65) Prior Publication Data
US 2015/0368709 A1 Dec. 24, 2015

(30) Foreign Application Priority Data
Oct. 31, 2012 (IT) .............................. TO2012A0962

(51) Int. Cl.
*C12Q 1/68* (2006.01)
(52) U.S. Cl.
CPC ......... *C12Q 1/6874* (2013.01); *C12Q 1/6806* (2013.01); *C12Q 1/6855* (2013.01); *C12Q 1/6858* (2013.01); *C12Q 1/6886* (2013.01); *C12Q 2600/156* (2013.01)
(58) Field of Classification Search
None
See application file for complete search history.

(56) References Cited

U.S. PATENT DOCUMENTS 6,420,117 B1  7/2002 Wessler et al.
2010/0267023 A1* 10/2010 Zabeau ................ C12Q 1/6855
435/6.12

FOREIGN PATENT DOCUMENTS

| EP | 1350853 A1 | 10/2003 |
| JP | 2007-521003 A | 8/2007 |
| JP | 2009-171934 A | 8/2009 |
| WO | WO 00/17390 A1 | 3/2000 |

OTHER PUBLICATIONS

Arneson et al., "Comparison of Whole Genome Amplification Methods for Analysis of DNA Extracted from Microdissected Early Breast Lesions in Formalin-Fixed Paraffin-Embedded Tissue," ISRN Oncol. (2012), vol. 2012, Article ID 710692, 10 pages.
Lee et al., "Comparison of Whole Genome Amplification Methods for Further Quantitative Analysis with Microarray-Based Comparative Genomic Hybridization," *Taiwan J. Obstet. Gynecol.*, (2008), 47(1):32-41.
Nie et al., "CYP1A1*2A polymorphism as a predictor of clinical outcome in advanced lung cancer patients treated with EGFR-TKI and its combined effects with EGFR intron 1 (CA)n polymorphism," *European Journal of Cancer*, (2011), 47:1962-1970.
Stoecklein et al., "SCOMP is Superior to Degenerated Oligonucleotide Primed-Polymerase Chain Reaction for Global Amplification of Minute Amounts of DNA from Microdissected Archival Tissue Samples," *American Journal of Pathology*, (2002), 161(1):43-51.
International Search Report issued in corresponding PCT Application No. PCT/IB2013/059827 dated Apr. 1, 2014, 5 pages.

* cited by examiner

*Primary Examiner* — Samuel C Woolwine
(74) *Attorney, Agent, or Firm* — Dorsey & Whitney LLP

(57) ABSTRACT

The present invention relates to a method for detecting a first and/or a second target DNA sequence from a DNA library, differing in that a mutation generates/eliminates a restriction site for a restriction endonuclease, comprising the steps of: (a) providing the DNA library, in which each of the DNA sequences comprises a first sequence segment, a second sequence segment of genomic DNA as cleaved by the restriction endonuclease, and a third sequence segment reverse complementary to the union of said first sequence segment and 5' overhang, if any, of the restriction endonuclease; (b) amplifying the library of DNA sequences by PCR using: a first reverse primer which hybridizes to the 3' end region of the second sequence segment of the first or second target sequence positive strand; a second forward primer which hybridizes to the 3' end region of the second sequence segment of the first target sequence antipositive strand; a third forward primer comprising a first portion hybridizing to the 5' end region of the third sequence segment of the second target sequence antipositive strand and a second portion hybridizing to the 3' end region of the second sequence segment of the second target sequence antipositive strand, wherein the first portion of the third forward primer has a length from 20% to 80% with respect to the total length of the third forward primer; (c) detecting DNA sequences amplified in step (b).

11 Claims, 14 Drawing Sheets

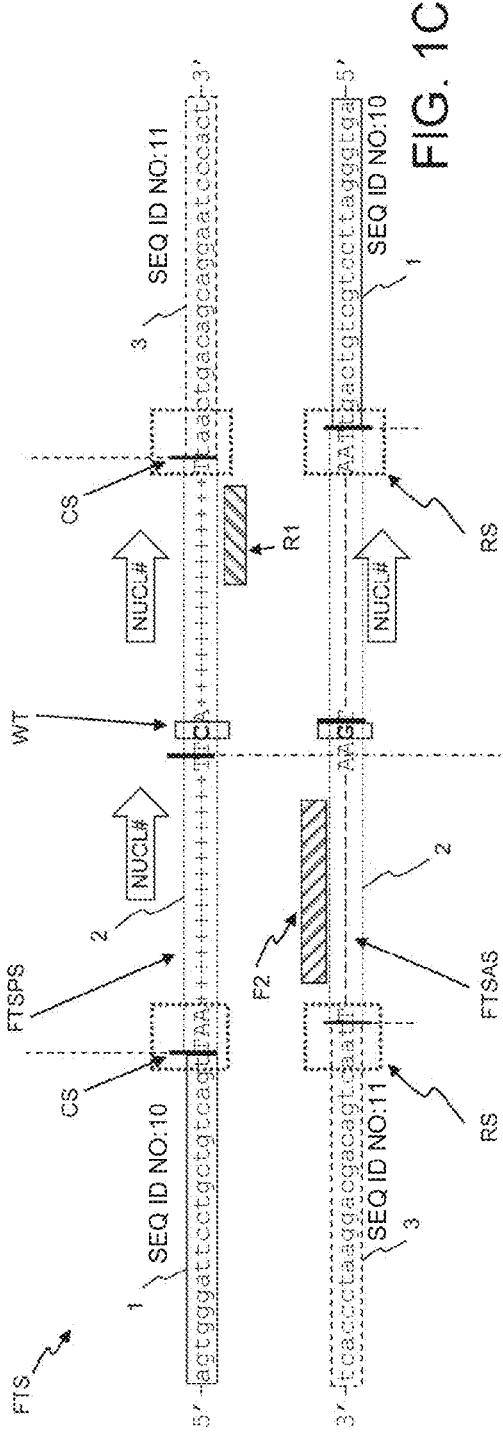
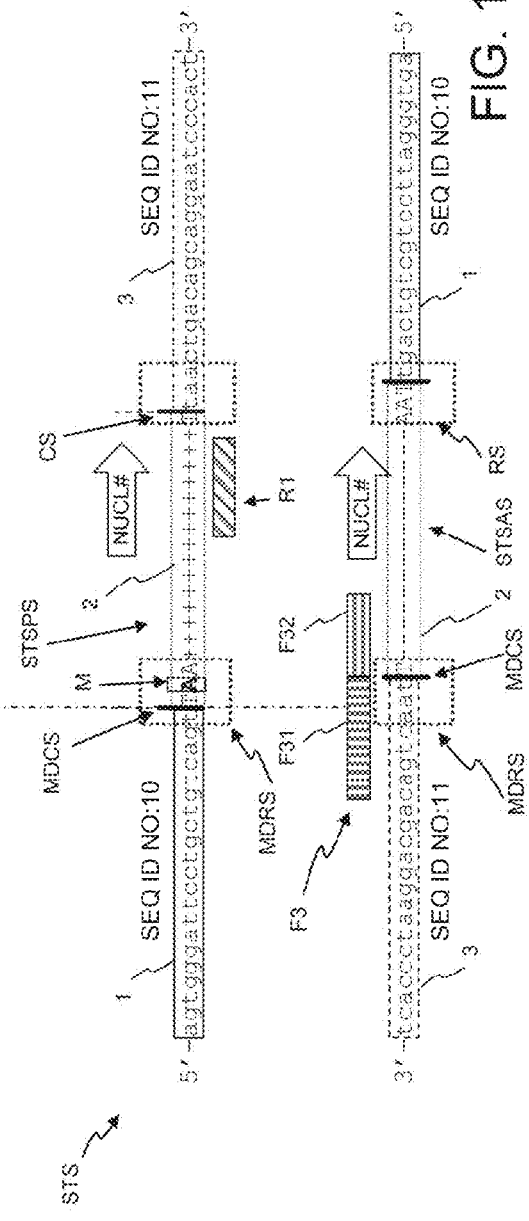
FIG. 1C
FIG. 1D

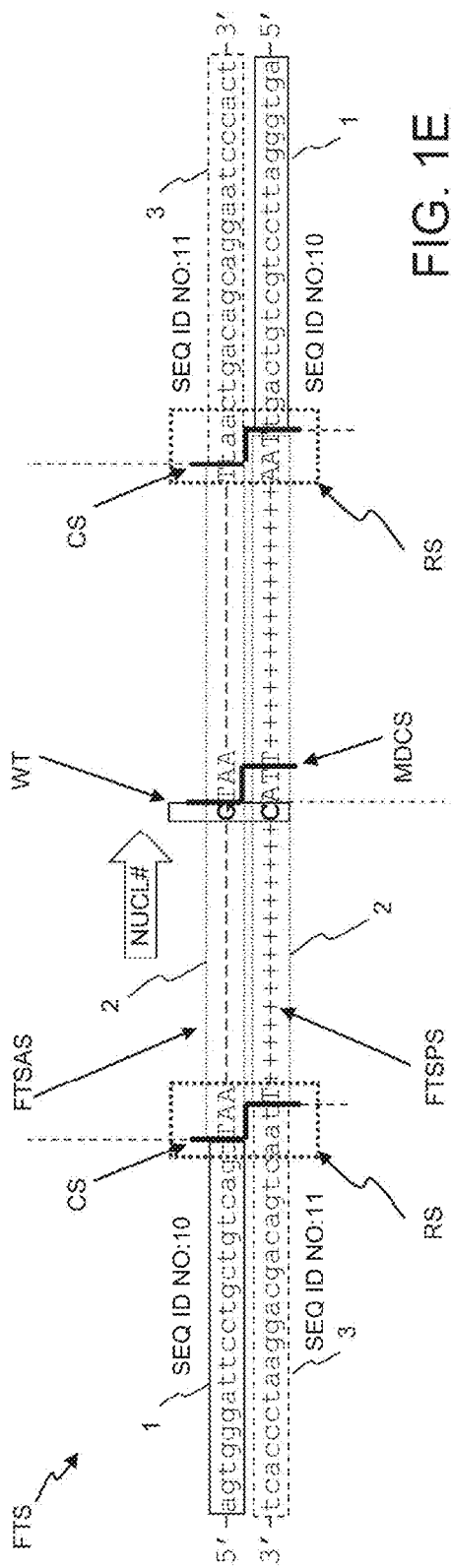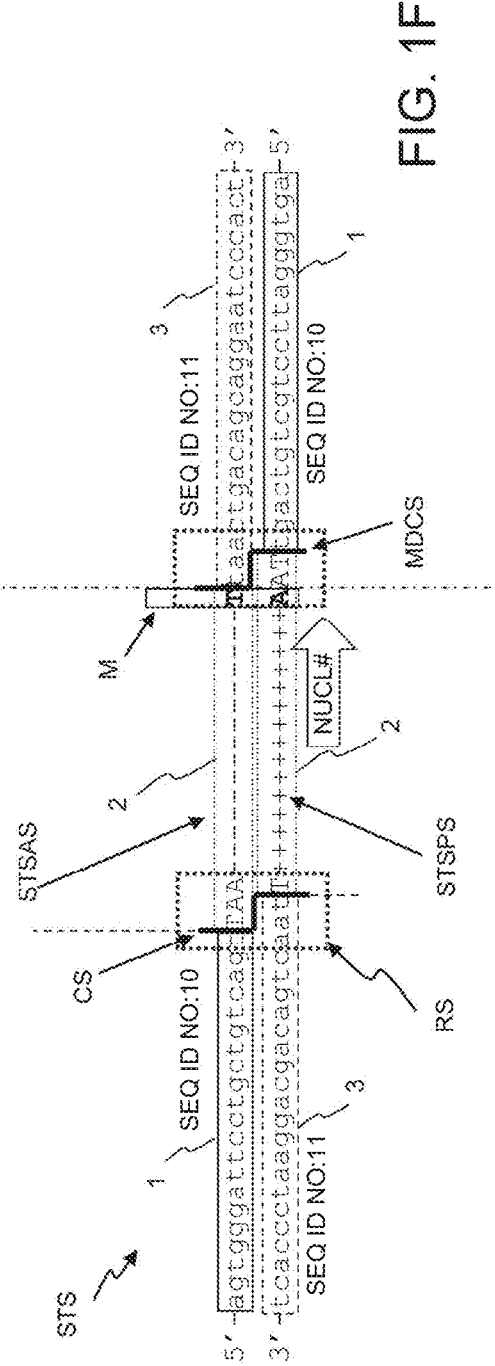

| Cell ID | Cell Type | # cell | Fixation | Permeabilization | ALK F1174 L | |
|---|---|---|---|---|---|---|
| | | | | | WT allele | M allele |
| AWG1152R1 | SY5Y | 1 | Live | na | 1 | 1 |
| AWG1152R2 | SY5Y | 1 | Live | na | 1 | 1 |
| AWG1152R3 | SY5Y | 1 | Live | na | 1 | 1 |
| AWG1152R4 | SY5Y | 1 | Live | na | 1 | 0 |
| AWG1152R5 | SY5Y | 1 | Live | na | 1 | 1 |
| AWG1152R6 | SY5Y | 1 | Live | na | 1 | 1 |
| AWG1152R7 | SY5Y | 1 | Live | na | 1 | 1 |
| AWG1152R8 | SY5Y | 1 | Live | na | 1 | 1 |
| AWG1152R9 | SY5Y | 1 | Live | na | 1 | 1 |
| AWG1152R10 | SY5Y | 1 | Live | na | 1 | 1 |
| AWG1157R1 | SY5Y | 1 | CYTO-CHEX | INSIDE PERM | 1 | 1 |
| AWG1157R2 | SY5Y | 1 | CYTO-CHEX | INSIDE PERM | 1 | 0 |
| AWG1157R3 | SY5Y | 1 | CYTO-CHEX | INSIDE PERM | 1 | 1 |
| AWG1157R4 | SY5Y | 1 | CYTO-CHEX | INSIDE PERM | 1 | 1 |
| AWG1157R5 | SY5Y | 1 | CYTO-CHEX | INSIDE PERM | 1 | 1 |
| AWG1157R6 | SY5Y | 1 | CYTO-CHEX | INSIDE PERM | 1 | 0 |
| AWG1157R7 | SY5Y | 1 | CYTO-CHEX | INSIDE PERM | 1 | 0 |
| AWG1157R8 | SY5Y | 1 | CYTO-CHEX | INSIDE PERM | 1 | 1 |
| AWG1157R9 | SY5Y | 1 | CYTO-CHEX | INSIDE PERM | 1 | 1 |
| AWG1157R10 | SY5Y | 1 | CYTO-CHEX | INSIDE PERM | 1 | 1 |
| AWG1159R1 | SY5Y | 1 | CYTO-CHEX | INSIDE PERM | 1 | 1 |
| AWG1159R3 | SY5Y | 1 | CYTO-CHEX | INSIDE PERM | 1 | 1 |
| AWG1159R4 | SY5Y | 1 | CYTO-CHEX | INSIDE PERM | 1 | 1 |
| AWG1159R5 | SY5Y | 1 | CYTO-CHEX | INSIDE PERM | 1 | 1 |
| AWG1159R6 | SY5Y | 1 | CYTO-CHEX | INSIDE PERM | 1 | 1 |
| AWG1159R7 | SY5Y | 1 | CYTO-CHEX | INSIDE PERM | 1 | 1 |
| AWG1159R8 | SY5Y | 1 | CYTO-CHEX | INSIDE PERM | 1 | 1 |
| AWG1159R9 | SY5Y | 1 | CYTO-CHEX | INSIDE PERM | 1 | 1 |
| AWG1159R10 | SY5Y | 1 | CYTO-CHEX | INSIDE PERM | 1 | 1 |
| AWG1153R1 | SY5Y | 1 | PFA 2% 20' RT | INSIDE PERM | 1 | 1 |
| AWG1153R2 | SY5Y | 1 | PFA 2% 20' RT | INSIDE PERM | 1 | 1 |
| AWG1153R3 | SY5Y | 1 | PFA 2% 20' RT | INSIDE PERM | 1 | 1 |
| AWG1153R4 | SY5Y | 1 | PFA 2% 20' RT | INSIDE PERM | 1 | 1 |
| AWG1153R5 | SY5Y | 1 | PFA 2% 20' RT | INSIDE PERM | 1 | 1 |
| AWG1153R6 | SY5Y | 1 | PFA 2% 20' RT | INSIDE PERM | 1 | 1 |
| AWG1153R7 | SY5Y | 1 | PFA 2% 20' RT | INSIDE PERM | 1 | 1 |
| AWG1153R8 | SY5Y | 1 | PFA 2% 20' RT | INSIDE PERM | 1 | 1 |
| AWG1153R9 | SY5Y | 1 | PFA 2% 20' RT | INSIDE PERM | 1 | 0 |
| AWG1153R10 | SY5Y | 1 | PFA 2% 20' RT | INSIDE PERM | 1 | 1 |
| AWG1158R1 | SY5Y | 1 | PFA 2% 20' RT | INSIDE PERM | 1 | 1 |
| AWG1158R2 | SY5Y | 1 | PFA 2% 20' RT | INSIDE PERM | 1 | 1 |
| AWG1158R3 | SY5Y | 1 | PFA 2% 20' RT | INSIDE PERM | 1 | 1 |
| AWG1158R4 | SY5Y | 1 | PFA 2% 20' RT | INSIDE PERM | 1 | 1 |
| AWG1158R5 | SY5Y | 1 | PFA 2% 20' RT | INSIDE PERM | 1 | 0 |
| AWG1158R6 | SY5Y | 1 | PFA 2% 20' RT | INSIDE PERM | 1 | 1 |
| AWG1158R7 | SY5Y | 1 | PFA 2% 20' RT | INSIDE PERM | 1 | 1 |
| AWG1158R8 | SY5Y | 1 | PFA 2% 20' RT | INSIDE PERM | 1 | 1 |
| AWG1158R9 | SY5Y | 1 | PFA 2% 20' RT | INSIDE PERM | 1 | 1 |
| AWG1106R1 | PBMC | 1 | PFA 2% 20' RT | INSIDE PERM | 1 | 0 |
| AWG1106R2 | PBMC | 1 | PFA 2% 20' RT | INSIDE PERM | 1 | 0 |
| AWG1162R1 | PBMC | 1 | Live | na | 1 | 0 |
| AWG1162R2 | PBMC | 1 | Live | na | 1 | 0 |

FIG. 10

| Cell ID | Cell Type | # cells | Fixation | EGFR Exon19 Del E746_A750 | |
|---|---|---|---|---|---|
| | | | | WT | M |
| AEX1204R1 | HCC-827 | 1 | Veridex | 1 | 1 |
| AEX1204R2 | HCC-827 | 1 | Veridex | 1 | 1 |
| AEX1204R3 | HCC-827 | 1 | Veridex | 1 | 1 |
| AEX1204R4 | HCC-827 | 1 | Veridex | 1 | 1 |
| AEX1204R5 | HCC-827 | 1 | Veridex | 1 | 1 |
| AEX1204R6 | HCC-827 | 1 | Veridex | 1 | 1 |
| AEX1204R7 | HCC-827 | 1 | Veridex | 1 | 1 |
| AEX1204R8 | HCC-827 | 1 | Veridex | 1 | 1 |
| AEX1204R9 | HCC-827 | 1 | Veridex | 1 | 1 |
| AEX1204R10 | HCC-827 | 1 | Veridex | 1 | 1 |
| AEX1171R1 | HCC-827 | 1 | Veridex | 1 | 1 |
| AEX1171R2 | HCC-827 | 1 | Veridex | 0 | 1 |
| AEX1171R3 | HCC-827 | 1 | Veridex | 1 | 1 |
| AEX1171R4 | HCC-827 | 1 | Veridex | 1 | 1 |
| AEX1171R5 | HCC-827 | 1 | Veridex | 1 | 1 |
| AEX1171R6 | HCC-827 | 1 | Veridex | 1 | 1 |
| AEX1171R7 | HCC-827 | 1 | Veridex | 1 | 1 |
| AEX1171R8 | HCC-827 | 1 | Veridex | 1 | 1 |
| AEX1171R9 | HCC-827 | 1 | Veridex | 1 | 1 |
| AEX1171R10 | HCC-827 | 1 | Veridex | 1 | 1 |
| AEX1346R1 | HCC-827 | 1 | Veridex | 1 | 1 |
| AEX1346R2 | HCC-827 | 1 | Veridex | 1 | 1 |
| AEX1346R3 | HCC-827 | 1 | Veridex | 1 | 1 |
| AEX1346R4 | HCC-827 | 1 | Veridex | 0 | 1 |
| AEX1346R5 | HCC-827 | 1 | Veridex | 1 | 1 |
| AEX1346R6 | HCC-827 | 1 | Veridex | 1 | 1 |
| AEX1346R7 | HCC-827 | 1 | Veridex | 1 | 1 |
| AEX1346R8 | HCC-827 | 1 | Veridex | 1 | 1 |
| AEX1346R9 | HCC-827 | 1 | Veridex | 1 | 1 |
| AEX1346R10 | HCC-827 | 1 | Veridex | 0 | 1 |
| AEX1346R11 | HCC-827 | 1 | Veridex | 1 | 1 |
| AWG1162R1 | PBMC | 1 | Live | 1 | 0 |
| AWG1162R2 | PBMC | 1 | Live | 1 | 0 |
| AWG1162R3 | PBMC | 1 | Live | 1 | 0 |
| AWG1162R5 | PBMC | 1 | Live | 1 | 0 |
| AWG1162R6 | PBMC | 1 | Live | 1 | 0 |
| AWG1162R7 | PBMC | 1 | Live | 1 | 0 |
| AWG1162R8 | PBMC | 1 | Live | 1 | 0 |
| AWG1205R1 | PBMC | 1 | Live | 1 | 0 |
| AWG1205R2 | PBMC | 1 | Live | 1 | 0 |
| AWG1205R3 | PBMC | 1 | Live | 1 | 0 |
| AWG1205R4 | PBMC | 1 | Live | 1 | 0 |
| AWG1205R5 | PBMC | 1 | Live | 1 | 0 |
| AWG1205R6 | PBMC | 1 | Live | 1 | 0 |
| AWG1205R7 | PBMC | 1 | Live | 1 | 0 |
| AWG1205R8 | PBMC | 1 | Live | 1 | 0 |
| AWG1205R9 | PBMC | 1 | Live | 1 | 0 |
| AWG1205R10 | PBMC | 1 | Live | 1 | 0 |
| AEX1204R11 | PBMC | 1 | Veridex | 1 | 0 |
| AEX1204R12 | PBMC | 1 | Veridex | 1 | 1 |
| AEX1204R13 | PBMC | 1 | Veridex | 1 | 1 |
| AEX1171R11 | PBMC | 1 | Veridex | 1 | 0 |
| AEX1171R12 | PBMC | 1 | Veridex | 1 | 0 |
| AEX1171R13 | PBMC | 1 | Veridex | 1 | 0 |
| AEX1171R14 | PBMC | 1 | Veridex | 1 | 0 |
| AEX1171R15 | PBMC | 1 | Veridex | 1 | 0 |
| AEX1346R14 | PBMC | 1 | Veridex | 1 | 0 |
| AEX1346R15 | PBMC | 1 | Veridex | 1 | 1 |
| AEX1346R16 | PBMC | 1 | Veridex | 1 | 0 |

FIG. 15

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial
<220> FEATURE:
<221> NAME/KEY: source
<222> LOCATION: 1..21
<223> OTHER INFORMATION: /mol_type="DNA"
      /note="universal WGA primer"
      /organism="Artificial"

<400> SEQUENCE: 1
agtgggattc ctgctgtcag t                                              21

<210> SEQ ID NO 2
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="DNA"
      /note="ALK_WT_F"
      /organism="Homo sapiens"

<400> SEQUENCE: 2
```
cctctctgct ctgcagcaaa t    21

<210> SEQ ID NO 3
<211> LENGTH: 22
<212> TYPE: DNA
<213> ORGANISM: Homo sapiens
<220> FEATURE:
<221> NAME/KEY: source
<222> LOCATION: 1..22
<223> OTHER INFORMATION: /mol_type="DNA"
      /note="ALK_WT_R"
      /organism="Homo sapiens"

<400> SEQUENCE: 3
tctctcggag gaaggacttg ag    22

<210> SEQ ID NO 4
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="DNA"
      /note="ALK_M1_F"
      /organism="Homo sapiens"

<400> SEQUENCE: 4
tgctgtcagt taaaccacca    20

<210> SEQ ID NO 5
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="DNA"
      /note="ALK_M1_R"
      /organism="Homo sapiens"

<400> SEQUENCE: 5
ggtctctcgg aggaaggact    20

<210> SEQ ID NO 6
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="DNA"
      /note="Ex19_M_F"
      /organism="Homo sapiens"

<400> SEQUENCE: 6
taaaattccc gtcgctatca a    21

<210> SEQ ID NO 7
<211> LENGTH: 22
<212> TYPE: DNA
<213> ORGANISM: Homo sapiens
<220> FEATURE:
<221> NAME/KEY: source
<222> LOCATION: 1..22
<223> OTHER INFORMATION: /mol_type="DNA"
      /note="Ex19_M_R"
      /organism="Homo sapiens"

<400> SEQUENCE: 7
tgtggagatg agcagggtct ag                                                            22

<210> SEQ ID NO 8
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="DNA"
      /note="Ex19_WT_F"
      /organism="Homo sapiens"

<400> SEQUENCE: 8
ctgtcagtta agagaagcaa catctcc                                                       27

<210> SEQ ID NO 9
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="DNA"
      /note="Ex19_WT_R"
      /organism="Homo sapiens"

<400> SEQUENCE: 9
agagcagctg ccagacatga g                                                             21

<210> SEQ ID NO 10
<211> LENGTH: 24
<212> TYPE: DNA
<213> ORGANISM: Artificial Sequence
<220> FEATURE:
<223> OTHER INFORMATION: universal WGA primer + restr. site

<400> SEQUENCE: 10
agtgggattc ctgctgtcag ttaa                                                          24

<210> SEQ ID NO 11
<211> LENGTH: 24
<212> TYPE: DNA
<213> ORGANISM: Artificial Sequence
<220> FEATURE:
<223> OTHER INFORMATION: reverse complementary to universal WGA primer +
      restr. site

<400> SEQUENCE: 11
tcaccctaag gacgacagtc aatt                                                          24

<210> SEQ ID NO 12
<211> LENGTH: 22
<212> TYPE: DNA
<213> ORGANISM: Homo sapiens

<400> SEQUENCE: 12
ctggtggttg aatttgctgc ag                                                            22

<210> SEQ ID NO 13
<211> LENGTH: 16
<212> TYPE: DNA

```
<213> ORGANISM: Homo sapiens

<400> SEQUENCE: 13
ctggtggttt aactga                                                       16

<210> SEQ ID NO 14
<211> LENGTH: 33
<212> TYPE: DNA
<213> ORGANISM: Homo sapiens

<400> SEQUENCE: 14
ctttcggaga tgttgcttct cttaactgac aga                                    33

<210> SEQ ID NO 15
<211> LENGTH: 29
<212> TYPE: DNA
<213> ORGANISM: Homo sapiens

<400> SEQUENCE: 15
ttcggagatg tcttgatagc gacgggaat                                         29

<210> SEQ ID NO 16
<211> LENGTH: 33
<212> TYPE: DNA
<213> ORGANISM: Homo sapiens

<400> SEQUENCE: 16
ttgcttctct taattccttg atagcgacgg gaa                                    33
```

METHOD AND KIT FOR DETECTING A WILD-TYPE AND/OR A MUTATED TARGET DNA SEQUENCE

This application is a national stage application under 35 U.S.C. § 371 of International Application No. PCT/IB2013/059827, filed Oct. 31, 2013, entitled "Method and Kit for Detecting a Wild-Type and/or A Mutated Target DNA Sequence," which claims priority to Italian Patent Application No. TO2012A000962, filed Oct. 31, 2012.

The present invention relates to a method and a kit for detecting a wt target DNA sequence and/or a mutated target DNA sequence, which differ in that a single or multiple nucleotide substitution or deletion or insertion generates/eliminates a restriction site for a restriction endonuclease.

A sequence listing submitted as an ASCII text file is hereby incorporated by reference. The file is named "1484-18 US amended sequence listing.txt," was created on Aug. 31, 2017, and contains 4 kilobytes.

STATE OF THE ART

Whole Genome Amplification on single or few cells is used to amplify DNA in order to allow different types of genetic analyses, including sequencing and SNP detection.

Whole Genome Amplification by means of a ligation-mediated PCR (LM-PCR) based on a deterministic restriction site (hereinafter referred to as DRS-WGA) is known from EP1109938.

DRS-WGA has been shown to be better for the amplification of single cells (see for example: Lee Y S, et al: Comparison of whole genome amplification methods for further quantitative analysis with microarray-based comparative genomic hybridization. Taiwan J Obstet Gynecol. 2008, 47(1):32-41) and also more tolerant to DNA degradation due to fixative treatment (see for example: Stoecklein N. H. et al: SCOMP is Superior to Degenerated Oligonucleotide Primed-PCR for Global Amplification of Minute Amounts of DNA from Microdissected Archival Samples. American Journal of Pathology 2002, Vol. 161, No. 1; Arneson N. et al.: Comparison of Whole Genome Amplification methods for analysis of DNA extracted from microdissected early breast lesions in formalin-fixed paraffin-embedded tissue. ISRN Oncol, 2012; 2012; 710692).

DRS-WGA DNA libraries comprise DNA fragments with the general structure shown in FIG. 1A. FIG. 1B shows a specific example of the structure of the DNA library fragments obtained by DRS-WGA using the restriction endonuclease MseI.

Mutation detection assays downstream of DRS-WGA are normally carried out by designing primers within the restriction endonuclease (RE) amplicon. Although DRS-WGA provides best results in terms of uniform and balanced amplification, designing assays to determine the presence of mutations may be challenging in circumstances in which the mutation at issue generates or eliminates a restriction site for the DRS-WGA restriction endonuclease within the RE amplicon, because the usual way to design primers within the RE amplicon does not allow distinguishing the wild-type and the mutated DNA.

By way of explanation, examples of mutations giving rise to the above mentioned problem are shown hereinafter for the restriction site TTAA of the MseI restriction endonuclease, however the same problems occur with any other restriction site. The following examples should not be intended as limiting of the present invention, as it may apply also to other methods for DRS-WGA, including methods using a restriction endonuclease yielding blunt end DNA fragments.

Case A. A Mutation Introduces a New Restriction Site (RS)
Substitution

A substitution is a DNA mutation where one (or more) nucleotide(s) is (are) wrongly replaced with a different nucleotide. This generates a change in the nucleotide sequence of the particular DNA site.

The substitution may therefore introduce a RS in the mutated (M) DNA sequence where no RS was present in the wild type (WT) DNA sequence.

As an example for a single base-substitution:

| WT Sequence | M Sequence | Case |
| --- | --- | --- |
| VTAA | TTAA | (1) |
| TVAA | TTAA | (2) |
| TTBA | TTAA | (3) |
| TTAB | TTAA | (4) | where V is A or C or G (not T), and B is C or G or T (not A).

Deletion

A DNA mutation may remove one (or more) nucleotide(s) producing a RS in the mutated (M) DNA sequence where no RS was present in the wild-type (WT) DNA sequence.

E.g. for single or multiple (n) base deletions:

| WT Sequence | M Sequence | Case |
| --- | --- | --- |
| T[V]$_n$TAA | TTAA | (5) |
| TT[V]$_n$AA | TTAA | (6) |
| TT[B]$_n$AA | TTAA | (7) |
| TTA[B]$_n$A | TTAA | (8) |

Insertion

A DNA mutation may insert one (or more) nucleotide(s) producing a RS in the mutated (M) DNA sequence where no RS was present in the wild type (WT) DNA sequence.

E.g. for a single base insertion:

| WT Sequence | M Sequence | Case |
| --- | --- | --- |
| VTAA | [insT]TAA | (9) |
| TTAB | TT[insA]AB | (10) | and the related indistinguishable cases of:

| VTAA | T[insT]AA | (9') |
| --- | --- | --- |
| TTAB | TTA[insA]B | (10') |

All of the above mutations introduce a RS, resulting in the mutation not being detectable in the DNA library fragment e.g. by PCR and Sequencing, when using primer pairs amplifying a region comprising the mutation site, as only the wild-type allele (if present) will be correctly amplified and sequenced. This situation is outlined in FIG. 2, Case A, left inset.

Case B. The Mutation Removes the Restriction Site from the Wild-Type (WT) Sequence Substitution A substitution may remove the RS present in the WT DNA sequence.

| WT Sequence | M Sequence | case |
| --- | --- | --- |
| TTAA | VTAA | (11) |
| TTAA | TVAA | (12) |
| TTAA | TTBA | (13) |
| TTAA | TTAB | (14) |

The above correspond to cases (1)-(4) where the M DNA sequence and the WT DNA sequence are swapped.

Deletion

A DNA mutation may remove one (or more) nucleotide(s) removing a RS where a RS was present in the wild type (WT) DNA sequence.

E.g. for single base deletions:

| WT Sequence | M Sequence | Case |
| --- | --- | --- |
| VTTAA | V[delT]TAA | (15) |
| TTAAB | TT[delA]AB | (16) | and the related indistinguishable cases of:

| VTTAA | VT[delT]AA | (15') |
| --- | --- | --- |
| TTAAB | TTA[delA]B | (16') |

Insertion

A DNA mutation may insert one (or more) nucleotide(s) removing a RS where a RS was present in the wild type (WT) DNA sequence.

| WT Sequence | M Sequence | Case |
| --- | --- | --- |
| TTAA | T[insV]$_n$TAA | (17) |
| TTAA | TT[insV]$_n$AA | (18) |
| TTAA | TT[insB]$_n$AA | (19) |
| TTAA | TTA[insB]$_n$A | (20) |

Any (and many other) cases comprising deletion of one or more bases as in the example above will remove the RS existing in a WT sequence, resulting in a non-digested sequence.

While the mutated sequence may readily be identified designing primer pairs amplifying the DNA sequence comprising the mutation site, the wild-type allele (if present) fails to be amplified, giving an incorrect assessment of the genotype. This situation is outlined in FIG. 2, Case B, right inset.

Moreover, when there is no mutation, there would be no signal at all from the PCR, and it would be impossible to determine whether there was a drop-out of the wild-type allele during DRS-WGA or the genotype is simply wild-type.

EP1350853 discloses the amplified fragment length polymorphism (AFLP) technique that reveals polymorphisms at restriction sites. The method for detecting sequence polymorphisms between one or more genomes comprises producing a nucleic acid fingerprint from said genomes by (a) providing from a starting nucleic acid a plurality of adaptor ligatable nucleic acid fragments with ends that are compatible to at least one adaptor, and wherein said nucleic acid fragments are obtained by fragmentation with restriction endonucleases; (b) performing a ligation reaction between said ends of said nucleic acid fragments and said at least one adaptor such as to produce adaptor-ligated nucleic acid fragments; (c) amplifying said adaptor-ligated nucleic acid fragments by using at least one amplification primer essentially complementary to the nucleotide sequence of said at least one adaptor; and (d) generating from said amplified adaptor-ligated nucleic acid fragments a nucleic acid fingerprint; comparing the obtained nucleic acid fingerprints for the presence or absence of, or differences between, amplified nucleic acid fragments such as to determine the presence of sequence polymorphisms.

This method however does not allow the detection of one specific polymorphic site.

An object of the present invention is therefore to provide a method for detecting a wild-type target DNA sequence and/or a mutated target DNA sequence in a library of DNA fragments having a structure such as that obtained by DRS-WGA, where the wild-type target DNA sequence and the mutated target DNA sequence differ in the presence of a restriction site for the restriction endonuclease of the DRS-WGA, that solves the above cited problems in a simple and efficient manner.

This object is achieved by the present invention as it relates to a method as defined in claim 1.

It is a further object of the present invention to provide a kit as defined in claim 10.

Definitions

Unless defined otherwise, all technical and scientific terms used herein have the same meaning as commonly understood by one of ordinary skill in the art to which this invention pertains. Although many methods and materials similar or equivalent to those described herein may be used in the practice or testing of the present invention, preferred methods and materials are described below. Unless mentioned otherwise, the techniques described herein for use with the invention are standard methodologies well known to persons of ordinary skill in the art.

By the term "restriction site" or "RS" there is intended the sequence of nucleotides (typically 4-8 base pairs in length) along a DNA molecule recognized by the restriction endonuclease (or "RE"). At the restriction site, the restriction endonuclease cleaves nucleotides by hydrolysing a phosphodiester bond between them.

By the term "mutation-dependent restriction site" (or "MDRS"), there is intended the RS which is introduced or removed by effect of the mutation.

By the term "cleavage site" (or "CS"), there is intended the position in the sequence of the restriction site in which the phosphodiester bonds hydrolysed by the RE are located.

By the term "mutation-dependent cleavage site" (or "MDCS"), there is intended the CS which is introduced or removed by effect of the mutation.

By the term "amplicon" there is intended a region of DNA produced by PCR amplification.

By the terms "DRS-WGA amplicon" or "WGA amplicon", there is intended a DNA fragment amplified during DRS-WGA, comprising a DNA sequence between two RS flanked by the ligated WGA primers.

By the terms "WGA PCR primer" or "universal WGA primer" or "adaptor", there is intended the additional oligonucleotide ligated to each fragment generated by the action of the restriction enzyme in DRS-WGA.

By the term "original DNA", there is intended the genomic DNA (gDNA) prior to amplification with DRS-WGA.

By the term "target sequence", there is intended the region of interest on the original DNA.

By the term "target sequence sense strand" there is generally intended the segment of the DNA strand running from 5'-3', which has the same sequence as the mRNA and is complementary to the antisense strand. The sense strand may also be referred to as "positive strand".

For the sake of simplicity, in the present description, the term "target sequence positive strand" (TSPS) will be used with the following meanings:
1) it identifies the genomic DNA sequence by increasing nucleotide number in the case in which the mutation occurs on the 3' side of the mutation-dependent cleavage site on the sequence with increasing nucleotide number
2) it identifies the reverse complementary of the genomic DNA sequence by increasing nucleotide number in the case in which the mutation occurs on the 5' side of the mutation dependent cleavage site position on the sequence with increasing nucleotide number Coherently, the term "target sequence antipositive strand" (TSAS) will be used in the present description with the following meanings:
3) it identifies the reverse complementary of the genomic DNA sequence by increasing nucleotide number in the case in which the mutation occurs on the 3' side of the mutation-dependent cleavage site on the sequence with increasing nucleotide number
4) it identifies the genomic DNA sequence by increasing nucleotide number in the case in which the mutation occurs on the 5' side of the mutation dependent cleavage site position on the sequence with increasing nucleotide number The expression "increasing nucleotide number" refers to numbering relative to the chromosome position (as found in sequence databases such as UCSC Genome Browser).

By the expression "5' end region of a sequence segment" there is intended that the localisation of the sequence of nucleotides referred to is towards the 5' terminal end of the sequence segment.

By the expression "3' end region of a sequence segment" there is intended that the localisation of the sequence of nucleotides referred to is towards the 3' terminal end of the sequence segment.

BRIEF DESCRIPTION OF THE DRAWINGS

FIG. 1C shows a sketch of the first target sequence positive and antipositive strands and location of related reverse and forward primers. Additional acronyms are as follows: R1=first reverse primer; F2=second forward primer.

FIG. 1D shows a sketch of the second target sequence positive and antipositive strands and location of related reverse and forward primers. Additional acronyms are as follows: F3=third forward primer; F31=first portion of third forward primer; F32=second portion of third forward primer.

FIG. 1E shows a sketch of the first target sequence positive and antipositive strands and location of related reverse and forward primers, when the mutation is located on the 5' side of the MDCS on the sequence by increasing nucleotide number.

FIG. 1F shows a sketch of the second target sequence positive and antipositive strands and location of related reverse and forward primers, when the mutation is located on the 5' side of the MDCS on the sequence by increasing nucleotide number.

In FIGS. 1A-1F, reference is made to the situation where the non-cleaved sequence is the WT sequence, and the cleaved sequence is the Mutant sequence. The alternative situation where the mutated sequence is non-cleaved and the wild-type sequence is cleaved can be readily obtained by simply swapping WT with M.

FIG. 4A shows the situation in which the mutation introduces a restriction site in the sequence. FIG. 4B shows the situation in which the mutation removes the restriction site in the sequence.

FIG. 10 shows a table summarising the results of Example 4.

FIG. 15 shows a table summarising the results of Example 6.

DETAILED DESCRIPTION OF THE INVENTION

Figure 2:
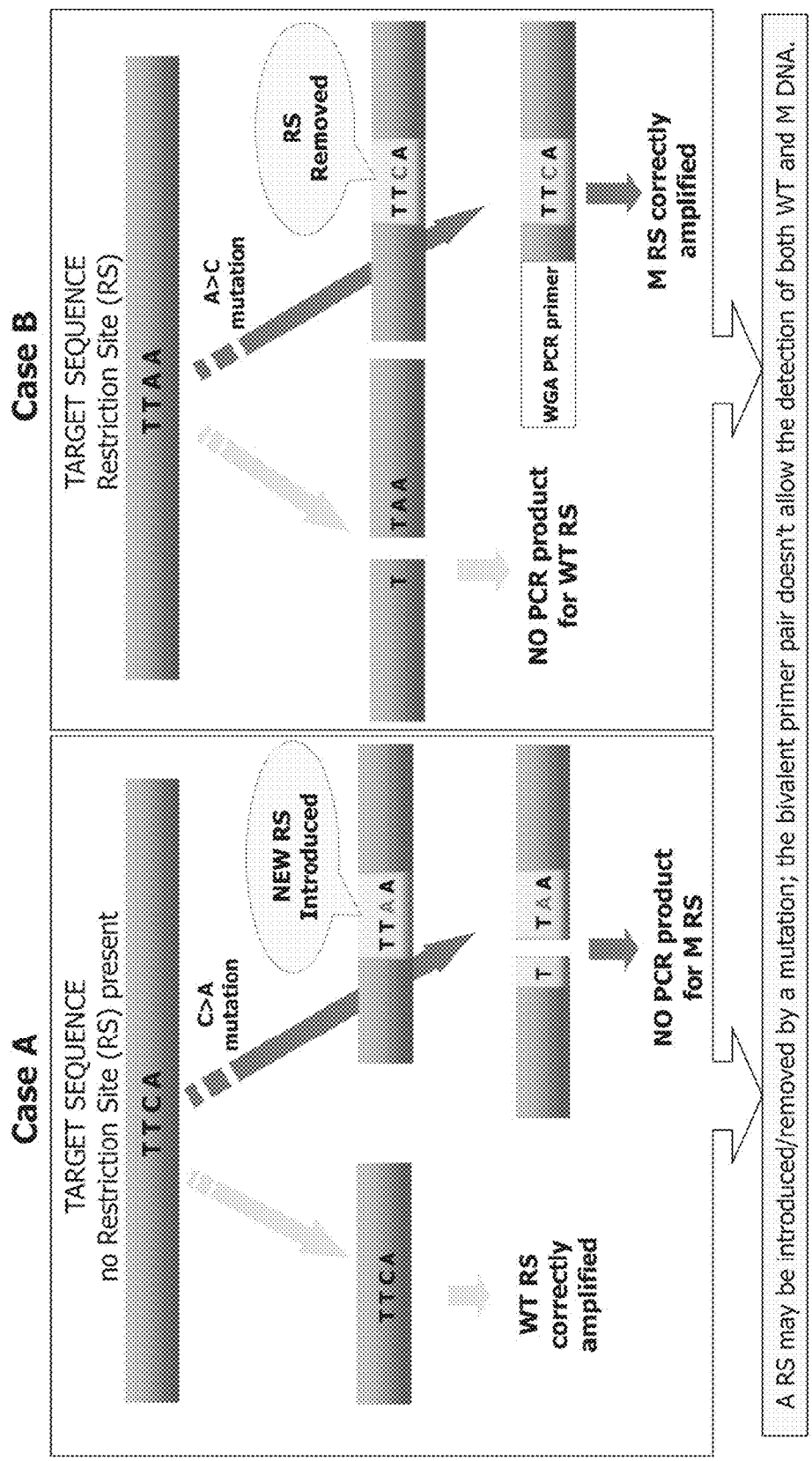
FIG. 2 shows a simplified sketch of the two situations comprising the introduction (Case A—left inset) or removal (Case B) of a restriction site in the mutated DNA sequence and the consequences with traditional mutation detection methods.

The method according to the present invention for detecting at least one of at least one first target DNA sequence and at least one second target DNA sequence from a library of DNA sequences comprises steps (a) to (c). The first target DNA sequence differs from the second target DNA sequence in that a single or multiple nucleotide substitution or deletion or insertion in the second sequence generates a restriction site for a restriction endonuclease. With reference to FIG. 2, case A, left inset, and FIG. 4A, the first target DNA sequence corresponds to the wild-type DNA sequence and the second target DNA sequence corresponds to the mutated DNA sequence, whereas with reference to FIG. 2, case B, right inset, and FIG. 4B, the first target DNA sequence corresponds to the mutated DNA sequence and the second target DNA sequence corresponds to the wild-type DNA sequence.

Figure 1A:
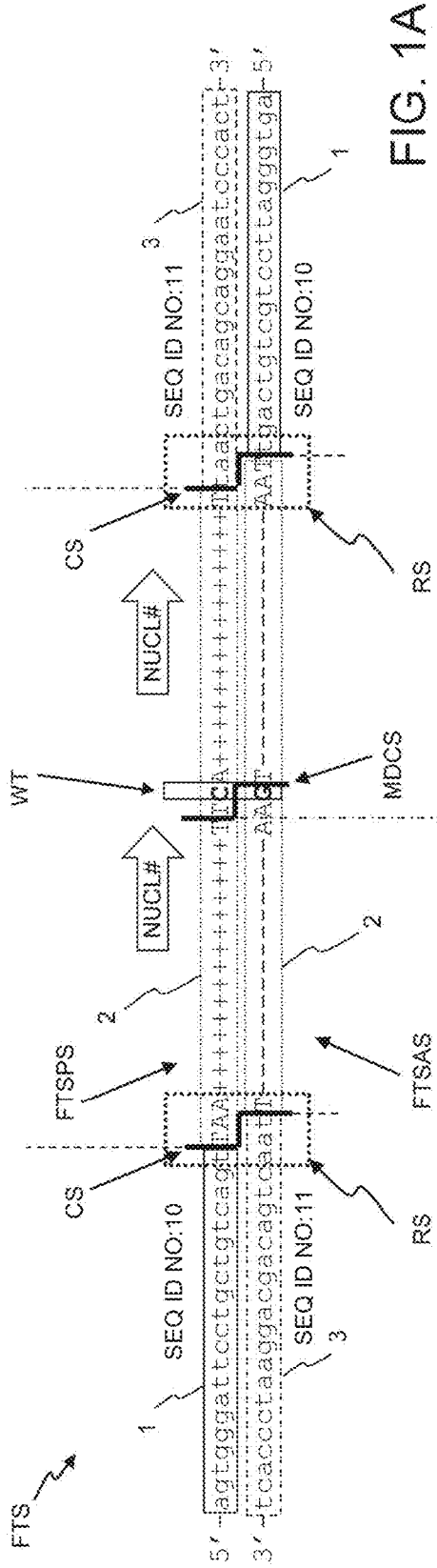
FIG. 1A shows a sketch of the general structure of a DNA library fragment obtained by a specific DRS-WGA, using the restriction endonuclease MseI, when a mutation dependent cleavage site (MDCS) is not cleaved. Acronyms are as follows: FTS=first target sequence; CS=cleavage site; RS=restriction site; FTSPS=first target sequence positive strand; FTSAS=first target sequence antipositive strand; NUCL#=nucleotide number (increasing according to the direction of the arrow); WT=wild-type; MDCS=mutation dependent cleavage site.
Figure 1B:
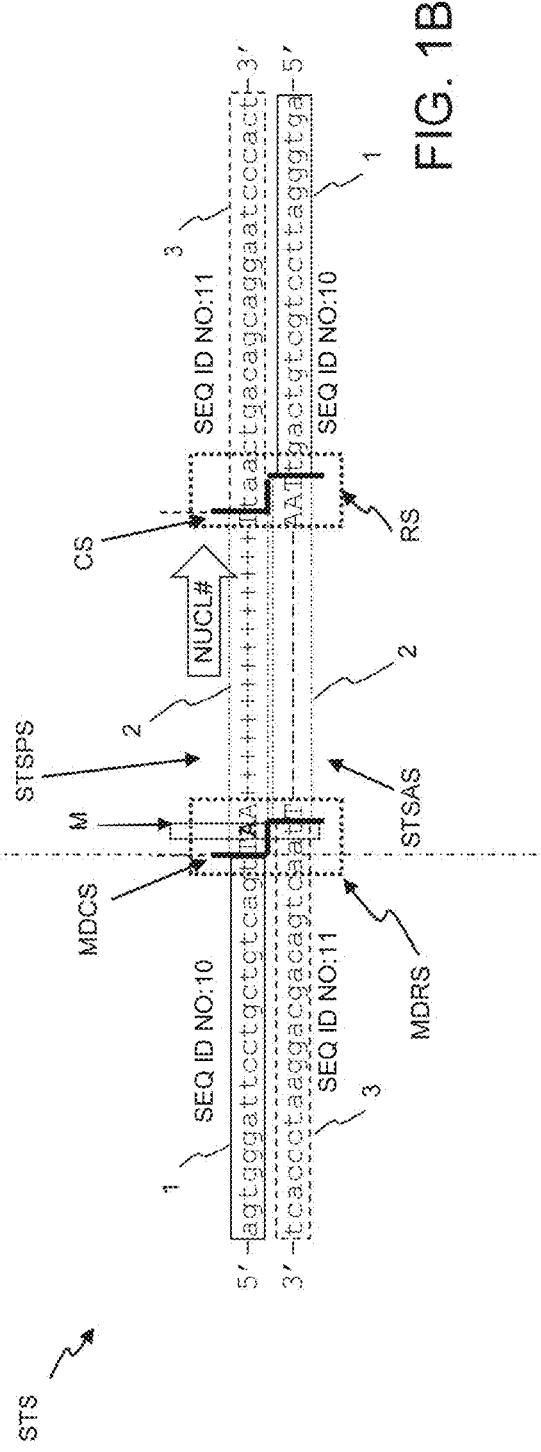
FIG. 1B shows a sketch of the general structure of a DNA library fragment obtained by a specific DRS-WGA, using the restriction endonuclease MseI, when a mutation dependent cleavage site (MDCS) is cleaved. Additional acronyms are as follows: STS=second target sequence; MDRS mutation dependent restriction site; M=mutated; STSPS=second target sequence positive strand; STSAS=second target sequence antipositive strand.

In step (a), the library of DNA sequences is provided. Each of the DNA sequences of the library comprises, respectively from the 5' end to the 3' end, a first sequence segment having a length from 15 to 50 nucleotides, a second sequence segment of genomic DNA as cleaved by the restriction endonuclease, and a third sequence segment reverse complementary to the union of the first sequence segment and, if any, the 5' overhang generated by the RE. With reference to FIG. 1A, numeral 1 shows the first sequence segment, numeral 2 shows the second sequence segment, and numeral 3 shows the third sequence segment. In a preferred embodiment the first sequence segment corresponds to the WGA PCR Primer.

The restriction endonuclease is preferably MseI.

In step (b), the library of DNA sequences is amplified by PCR using:
- at least one first reverse primer which hybridises to the 3' end region of the second sequence segment of the at least one first or second target sequence positive strand;
- at least one second forward primer which hybridises to the 3' end region of the second sequence segment of the at least one first target sequence antipositive strand;
- at least one third forward primer comprising a first portion hybridising to the 5' end region of the third sequence segment of the at least second target sequence antipositive strand and a second portion hybridising to the 3' end region of the second sequence segment of the at least one second target sequence antipositive strand, wherein the first portion of the at least one third forward primer has a length from 20% to 80% with respect to the total length of the at least one third forward primer.

The third forward primer is hereinafter sometimes referred to in short as "hybrid primer".

Preferably, at least one fourth reverse primer which hybridises to the 3' end region of the second sequence segment of the at least one second target sequence positive strand is used in step (b).

Preferably, the first portion of the at least one third forward primer has a length from 40 to 60%, with respect to the total length of the at least one third forward primer.

Preferably, the second portion of the at least one third forward primer has a length in bases comprised between a minimum corresponding to the consensus sequence of the restriction endonuclease minus, if any, the 5' overhang generated by the restriction endonuclease, all divided by two, and a maximum of 30 bases.

Figure 4A:
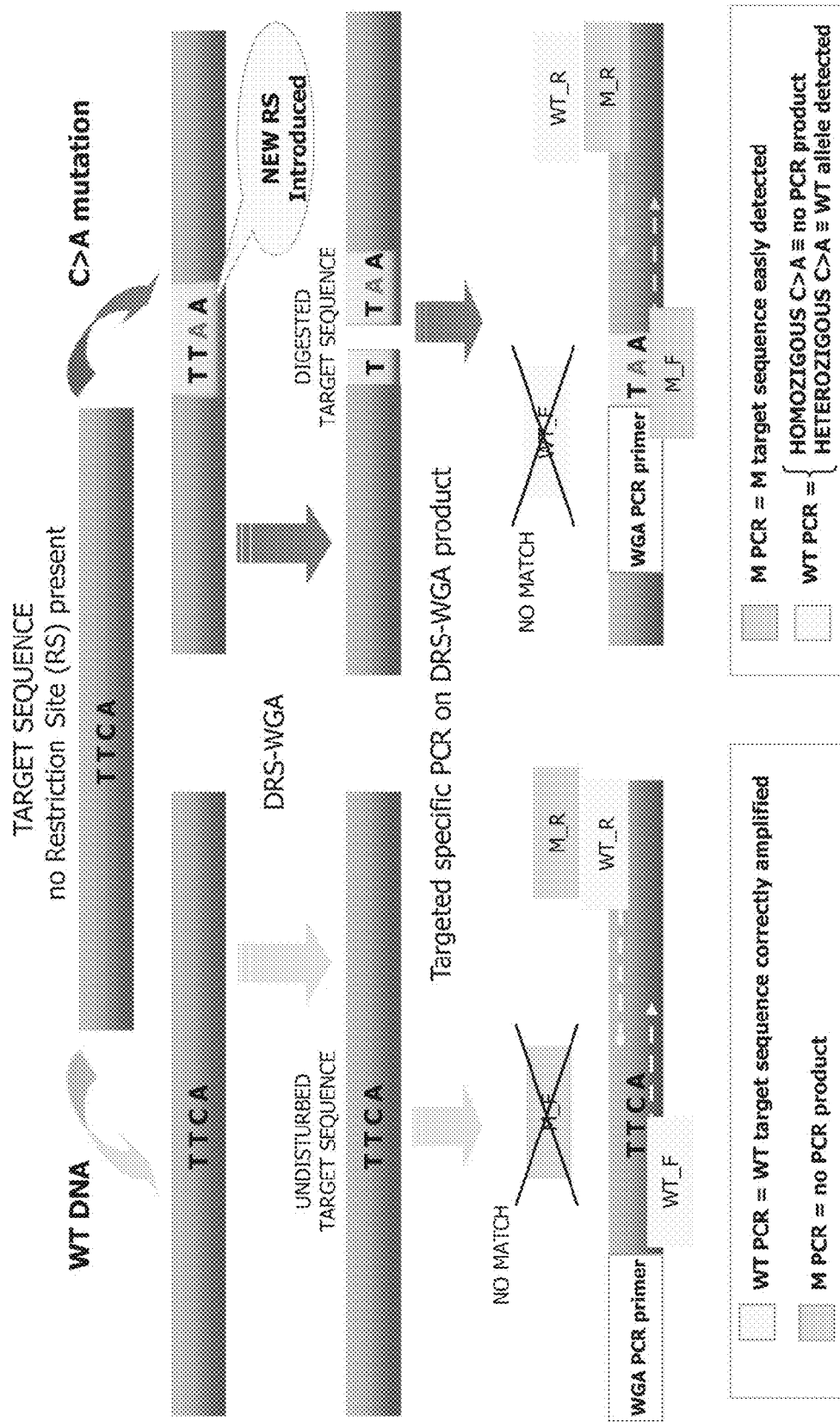
FIGS. 4A and 4B shows simplified sketches of the working principle of the method according to the invention.

With reference to FIG. 4A, the first reverse primer corresponds to the wild-type reverse primer (WT_R), the second forward primer corresponds to the wild-type forward primer (WT_F), the third forward primer corresponds to the mutated forward primer (M_F). In one embodiment, the first reverse primer serves to amplify not only the first, but also the second target sequence positive strand. In a preferred embodiment, however, a fourth reverse primer which differs from the first reverse primer, is used to amplify the second target sequence positive strand. In FIG. 4A, the fourth reverse primer corresponds to the mutated reverse primer (M_R).

Figure 4B:
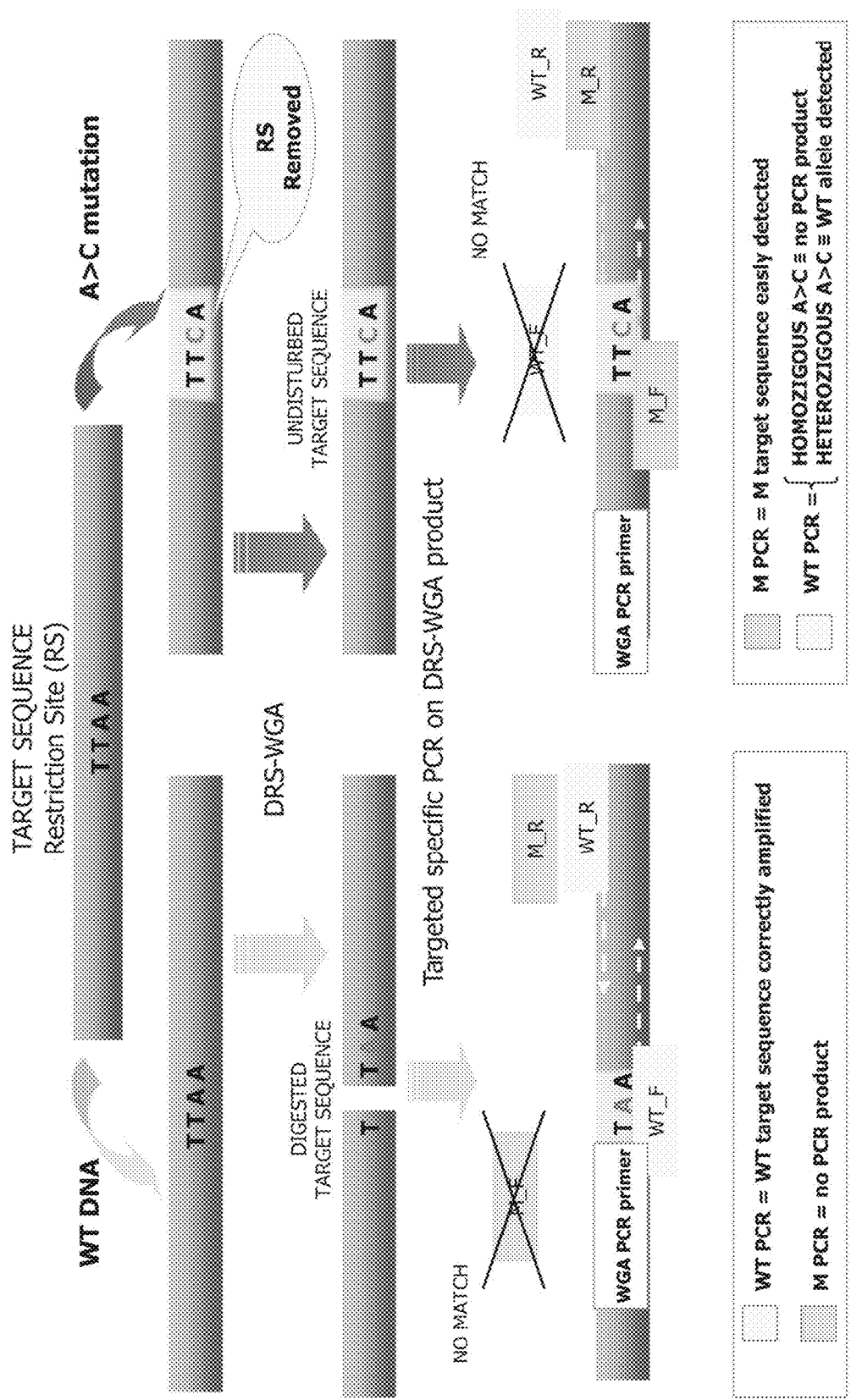

The same principle applies in FIG. 4B, where the first reverse primer corresponds to the mutated reverse primer (M_R), the second forward primer corresponds to the mutated forward primer (M_F), the third forward primer corresponds to the wild-type forward primer (WT-F), and the fourth reverse primer corresponds to the wild-type reverse primer (WT_R).

In step (c), the DNA sequences amplified in step (b) are detected. Step (c) may be performed by several detection methods known in the art, for example gel electrophoresis, capillary electrophoresis, DNA sequencing. Preferably, step (c) is performed by a DNA sequencing method. Even more preferably, the DNA sequencing method is Sanger sequencing, or sequencing by synthesis.

The method of the present invention may be used with any library of DNA sequences having the structure shown in FIG. 1A. The method is preferably used with a library of DNA sequences obtained by deterministic restriction site whole genome amplification.

According to the present invention there is also provided a kit comprising a first and/or a second and/or a third primer as defined above.

More specifically, the kit for detecting at least one of at least one first target DNA sequence and at least one second target DNA sequence from a library of DNA sequences, wherein the first target DNA sequence differs from the second target DNA sequence in that a single or multiple nucleotide substitution or deletion or insertion in the second sequence generates a restriction site for a restriction endonuclease, and wherein each of the DNA sequences of the library comprises, respectively from the 5' end to the 3' end, a first sequence segment having a length from 15 to 50 nucleotides, a second sequence segment of genomic DNA as cleaved by the restriction endonuclease, and a third sequence segment reverse complementary to the union of the first sequence segment and, if any, the 5' overhang generated by the restriction endonuclease, comprises:
- at least one first reverse primer which hybridises to the 3' end region of the second sequence segment of the at least one first or second target sequence positive strand;

at least one second forward primer which hybridises to the 3' end region of the second sequence segment of the at least one first target sequence antipositive strand;

at least one third forward primer comprising a first portion hybridising to the 5' end region of the third sequence segment of the at least second target sequence antipositive strand and a second portion hybridising to the 3' end region of the second sequence segment of the at least one second target sequence antipositive strand, wherein the first portion of the at least one third forward primer has a length from 20% to 80% with respect to the total length of the at least one third forward primer.

The kit preferably further comprises at least one fourth reverse primer which hybridises to the 3' end region of the second sequence segment of the at least one second target sequence positive strand.

The kit may be used to detect any kind of mutation generating or eliminating a restriction site for the restriction endonuclease of the ends of the second sequence segment of the DNA fragments of the library. The kit is preferably used in the diagnosis of mutations in the (anaplastic lymphoma kinase) ALK or (epidermal growth factor receptor) EGFR or (phosphatidylinositol 3-kinase catalytic alpha polypeptide) PIK3CA gene.

EXAMPLES

Example 1

Bivalent Primer Approach

Preliminary tests were carried out on SY5Y cell lines (SH-SY5Y ATCC Catalog No. CRL-2266™), which harbour a heterozygous C to A substitution at codon 1174 of the ALK gene, turning a Phenylalanine into a Leucine (F1174L); considering the flanking sequence, the heterozygous substitution introduces one new restriction site (RS) in the mutated allele, whereas the wild type allele does not have any RS.

FIG. 2 is a simplified sketch of the sequences and transformations in the WGA DNA library produced by the mutation.

To detect mutations occurring on the RS, the following approach was tested. The universal primer of the whole genome amplification (DRS-WGA primer, SEQ ID NO:1 having sequence AGTGGGATTCCTGCTGTCAGT) was exploited to design a 5' primer in a new PCR primer pair where the 3' primer overlaps a region in 3' with respect to the RS. The strategy consisted in designing a bivalent primer pair comprising:

a 5' primer having 95% homology with the DRS-WGA primer; and a 3' PCR primer which should provide the specificity required to the PCR, to selectively amplify the target region instead of other DRS-WGA amplicons.

This bivalent primer pair should in theory serve for the amplification of wild-type (WT) sequence and mutant (M) sequence.

Figure 3:
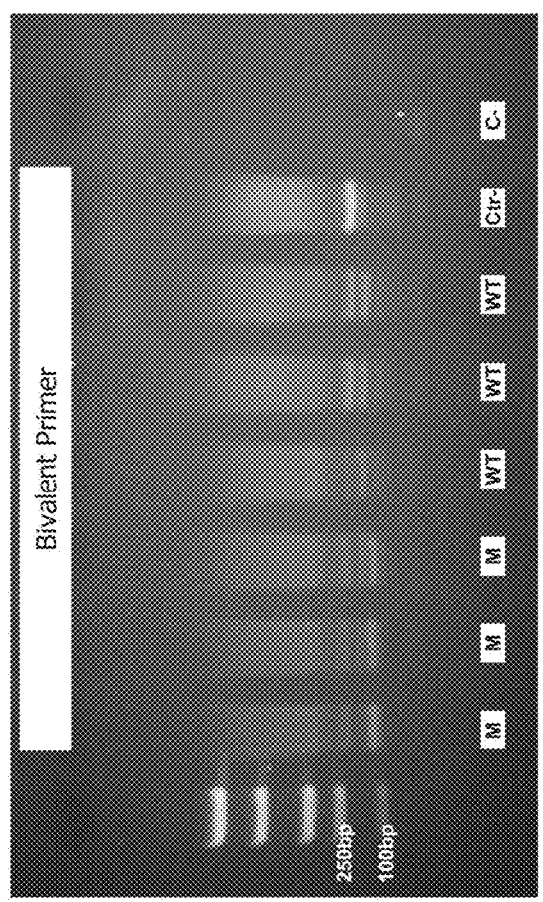
FIG. 3 shows an image of a gel electrophoresis of the separated products of a PCR amplification performed with a bivalent primer pair for wt and mutated DNA of Example 1. Cnt: blank of WGA reaction. C−: blank of PCR reaction.

Experimental evidence shows that this approach results to be poor and improper, and cannot guarantee the detection of the mutation at the RS. As shown in FIG. 3, the use of a bivalent primer provides unspecific amplification, which results in many amplification bands having different sizes, and no clearly distinguishable bands of the expected size (e.g. on single SY5Y cells, bearing a F1174L heterozygous mutation, isolated with DEPArray™ and amplified with DRS-WGA. 132 bp for the mutated sequence, 169 bp for the WT sequence). The amplification failed to give a clear and specific band both in mutated (M), wild-type (WT) and PCR negative control (C−) samples. The negative control of WGA (Ctr−), shows just an unspecific band.

One factor contributing to this poor result is that the 5' bivalent primer which corresponds by 95% to the ligated WGA-primer, is present on all DNA fragments of the DRS-WGA library, and the 3' bivalent primer does not provide the PCR reaction with sufficient specificity.

As an example, the human genome reference (*Homo Sapiens* hg 19) comprises 3,095,693,981 bases. If the genome is digested with a restriction endonuclease with a four base restriction site (e.g. TTAA), the mean length of the DNA fragments generated is 4 (the possible bases) to the power of 4 (the digestion sequence length considered) 256. The generated DNA library would thus comprise approximately 3,095,693,981/256~12.1 million different fragments, with a simplified assumption of a random sequence of the nucleotides in the DNA. All of them would comprise the same 5' primer (corresponding to the WGA-primer from the primary PCR).

The use of the bivalent primer pair therefore gives unspecific bands.

Example 2

Hybrid Primer Homology Range Limit

Amplification tests were carried out on the same SY5Y cell line as that used in Example 1, but using the method of the present invention.

To test the amplification of both wild-type (WT) and mutated (M) alleles in DRS-WGA products, individual SY5Y cells were isolated with DEPArray™, which provides pure single cells.

Figure 5:
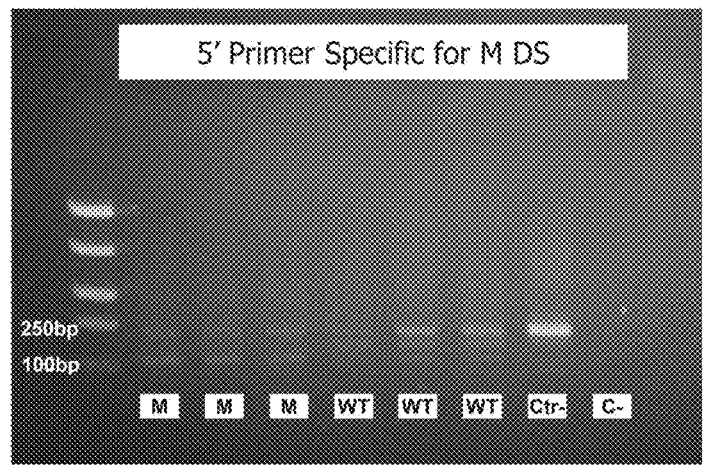
FIG. 5 shows an image of a gel electrophoresis of the separated products of a PCR amplification performed with a mutated specific 5'primer including the restriction site, homologous by 86% of its length to the universal WGA primer.

The amplification approach of using one 5' PCR primer matching the WGA universal primer by 86% its length provided a solution for the amplification neither of the WT nor of the M allele. As shown in FIG. 5, the amplification failed to give a clear and specific band both in mutated (M), wild-type (WT) and PCR negative control (C−) samples. The negative control of WGA (Ctr−), shows just an unspecific band.

Primers having different percentages of homology with the WGA universal primer were tested. The results are summarised in following Table 1.

TABLE 1

| Primer | Homology to the WGA-primer | | Homology to Original DNA | | F32 [# of basis] | TEST |
| --- | --- | --- | --- | --- | --- | --- |
| Universal | 21/22 | 95% | 1/22 | 5% | 0 | KO |
| Mutant 1 | 19/22 | 86% | 3/22 | 14% | 1 | KO |
| Mutant 2 | 10/20 | 50% | 10/22 | 50% | 8 | OK |
| Mutant 3 | 14/22 | 64% | 8/22 | 36% | 6 | OK |

In Table 1, column F32 reports the length in number of bases of the "second portion of third forward primer" i.e. the primer portion which has the same sequence as the original DNA, excluding the restriction endonuclease overhang.

It is clear from the results of Table 1 that a balanced compromise needs to be identified to meet the method requirements. Several tests have shown that the ideal percentage of identity of the hybrid primer with the WGA universal primer is from 20% to 80%, with an even better efficiency in the range from 40% to 60%.

Example 3

Introduction of a New RS in the Mutant Allele (ALK Gene)—Assay Design

The method according to the invention guarantees amplification (and sequencing) even in the case of incomplete digestion by the restriction endonuclease. In fact, the activity of the restriction endonuclease is not guaranteed for all the RS in the target DNA, and statistically a small percentage of undigested RS is present in the DRS-WGA, which nevertheless are successfully amplified by DRS-WGA, albeit with the WGA-primer (primary—PCR) being in another RS.

In case of an undigested site the use for the mutation assay of just one primer pair designed for the mutant sequence would not allow the amplification and the sequencing of the target.

Amplification tests were again carried out on the SY5Y cell line, which—as previously disclosed—harbours a heterozygous C to A substitution at codon 1174, turning a Phenylalanine into a Leucine (F1174L). The heterozygous substitution thus introduces a new RS in the mutated allele, whereas the wild-type allele does not have any RS.

The PCR primer sequences used for the amplification of WT and M alleles are shown in Table 2. For mutant allele forward primer, the first portion of the primer sequence homologous to the WGA primer is shown in bold and underlined, while the second portion of the primer which has the same sequence as the original DNA, excluding the restriction endonuclease overhang, (F32=8 basis) is shown boxed.

TABLE 2

| Primer Name | Sequence |
| --- | --- |
| ALK_WT_F SEQ ID NO: 2 | 5' CCTCTCTGCTCTGCAGCAAAT 3' |
| ALK_WT_R SEQ ID NO: 3 | 5' TCTCTCGGAGGAAGGACTTGAG 3' |
| ALK_M1_F SEQ ID NO: 4 | 5' TGCTGTCAGTTAACCACCA 3' |
| ALK_M1_R SEQ ID NO: 5 | 5' GGTCTCTCGGAGGAAGGACT 3' |

To test the amplification of both WT and M alleles in DRS-WGA products, individual SY5Y cells were isolated with DEPArray™, which provides pure single cells.

As negative control for the mutation detection, individual lymphocytes where also isolated with DEPArray™ and amplified with DRS-WGA.

The PCR amplification of the WT allele on both WT (lymphocytes) and heterozygous M (SY5Y) was achieved perfectly by the use of the specifically designed WT 5' primer, which allows the exclusive amplification of the WT allele.

Figure 6:
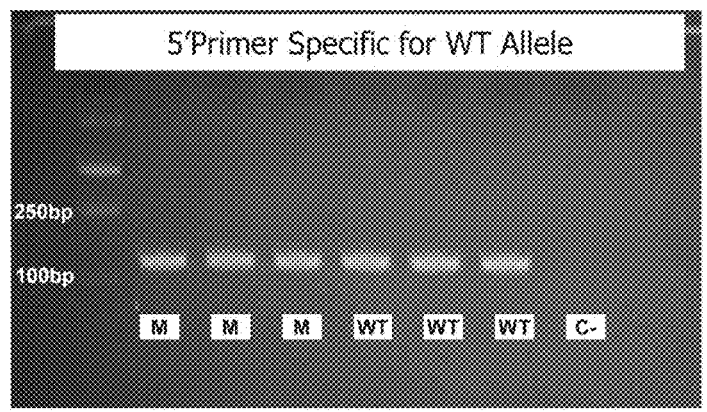
FIG. 6 shows an image of a gel electrophoresis of the separated products of a PCR amplification performed with the wild-type specific 5'primer of Example 3.

As can be observed in FIG. 6, there are no aspecific amplification products. Instead, the expected PCR band (132 bp) is clearly distinguishable.

The M-specific 5' primer was tested for the same lymphocytes and SY5Y cells to detect the specificity of the amplification provided by the primer designed straddling the target sequence and the universal DRS-WGA primer.

Figure 7:
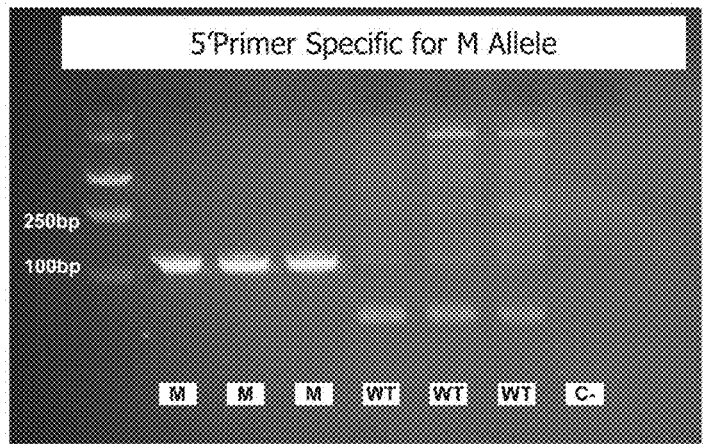
FIG. 7 shows an image of a gel electrophoresis of the separated products of a PCR amplification performed with the mutated specific 5'primer of Example 3.

As may be seen in FIG. 7, in this case, as expected, the specific amplification was obtained only in the SY5Y single cell DRS-WGA DNA. DRS-WGA DNA from lymphocytes, being WT for the target mutation, was negative for the expected amplification, and only unspecific PCR amplifications were present.

Figure 8:
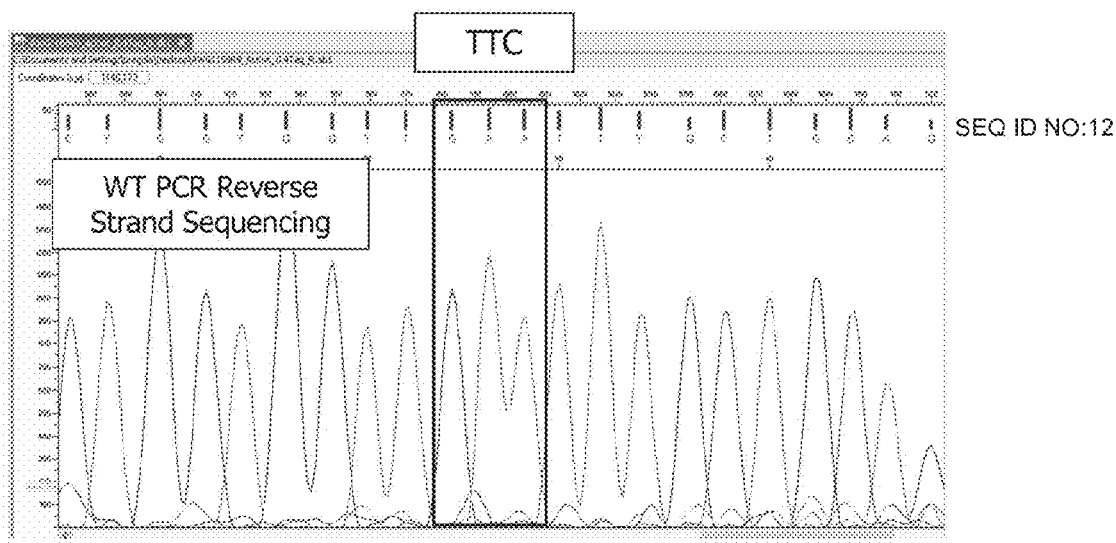
FIG. 8 shows an example of sequencing of a wild-type allele of Example 3.
Figure 9:
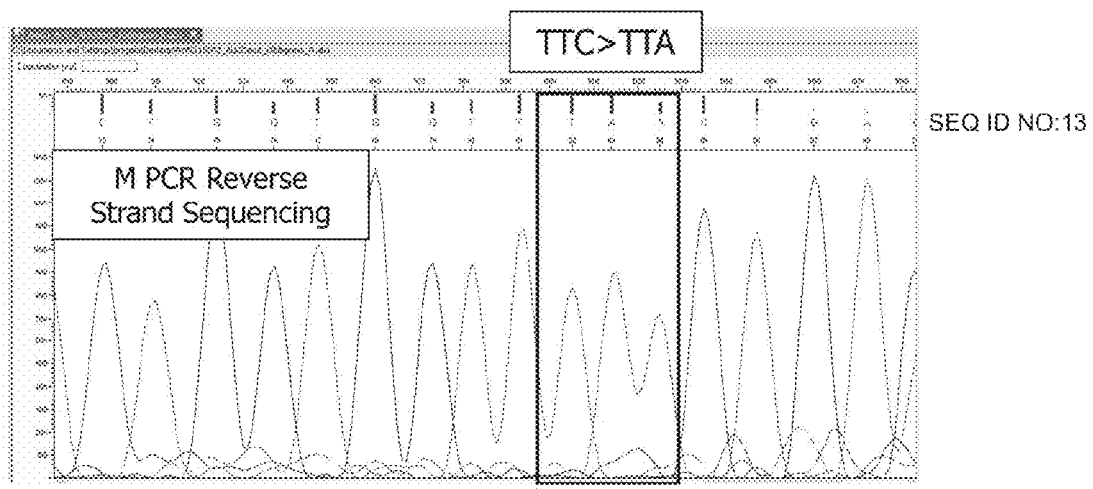
FIG. 9 shows an example of sequencing of a mutated allele of Example 3.

To demonstrate that the amplification achieved was specific and allowed sequencing, all the amplification products were sequenced from their 3' end. The corresponding WT or M status was confirmed for all amplification products showing the specificity achieved with the described method. An example of sequencing of a WT allele is shown in FIG. 8, whereas an example of sequencing of a M allele is shown in FIG. 9.

Results are summarised in Table 3.

TABLE 3

| | Single Cells Replicates | Sequence obtained with M-Specific 5'primer | Sequence obtained with WT-Specific 5'primer |
| --- | --- | --- | --- |
| WBC | 1 | No PCR Product | WT |
| | 2 | No PCR Product | WT |
| | 3 | No PCR Product | WT |
| SY5Y | 1 | M | WT |
| | 2 | M | WT |
| | 3 | M | WT |

In a preferred embodiment, the second portion (F32) of the third forward primer (F3) is shorter than 30 nucleotides so as not to mis-prime on the first target sequence antipositive strand (FTSAS)—i.e. the wild-type sequence in this example—, thus starting a PCR reaction which may result in a false-positive (as per its PCR product length and sequence). More preferably, the length of the second portion (F32) is shorter than 20 nucleotides. Even more preferably, the length of said second portion (F32) of said third forward primer (F3) is shorter or equal to 10 nucleotides.

The second portion (F32) of the third forward primer (F3) should not be too short as to not provide enough specificity, (see for example results in table I). In particular the length of said second portion of the third forward primer, should be greater than the restriction site consensus sequence length minus the length of the 5' overhang of the digested DNA, all divided by two. In order to obtain a greater specificity, the second portion (F32) of the third forward primer (F3) should be at least 3 nucleotides, and even more preferably at least 6 nucleotides, longer than the restriction site consensus sequence length minus the length of the 5' overhang of the digestd DNA, all divided by two.

Example 4

Introduction of a New RS in the Mutant Allele (ALK Gene)—Assay Validation

The method described above has been further validated with 54 single cells:
  10 single live, fresh SY5Y;
  19 single SY5Y, previously fixed with 2% paraformaldehyde (PFA) 20 minutes at room temperature, and permeabilised with Inside Perm (Miltenyi Biotec);
  19 single SY5Y, previously fixed with CytoChex™, and permeabilised with Inside Perm;
  2 single fresh, live lymphocytes;
  2 single lymphocytes, previously fixed with 2% PFA 20 minutes at room temperature, and permeabilised with Inside Perm (Miltenyi Biotec).

The method amplified the WT allele in 100% of SY5Y and lymphocytes cells, and the mutant allele was amplified in 9/10=90% of live SY5Y, 16/19=84% of SY5Y cells fixed & permeabilised with cyto-chex/inside-perm, 17/19=89% of SY5Y cells fixed & permeabilized with PFA 2% 20' @ room temperature/inside-perm, and 0/4=0% of lymphocytes.

Results are shown in FIG. 10 and summarised in Table 4.

TABLE 4

| | | ALK | |
|---|---|---|---|
| | | PCR of WT Allele | PCR of F1174L M Allele |
| SY5Y | Live | 100% | 90% |
| | CytoChex, Inside Perm | 100% | 84% |
| | PFA, Inside Perm | 100% | 89% |
| Lymphocytes | Live | 100% | 0% |
| | PFA, Inside Perm | 100% | 0% |

These results show the efficacy and robustness of the method of the present invention on larger numbers of samples.

Example 5

Removal of a RS in the Mutant Allele (EGFR Gene)—Assay Design

Amplification tests were carried out on the HCC-827 cell line, harbouring a deletion of 5 codons in the EGFR gene. The deletion removes a restriction site (RS), allowing the detection of the M allele, but not of the WT allele which has the RS, when using a single PCR and primer pairs on the human genome.

Individual HCC-827 cells were isolated with DEPArray™, along with lymphocytes as a control of the WT condition.

Two different primer pairs targeted for the M allele (with the deleted RS) and WT allele (still maintaining the RS) were designed and led to the correct identification of both WT and M conditions.

The PCR primer sequences used for the amplification of WT and M alleles are shown in Table 5. For wild-type allele forward primer, the first portion of the primer sequence homologous to the WGA primer is shown in bold and underlined, while the second portion of the primer which has the same sequence as the original DNA, excluding the restriction endonuclease overhang, (F32=16b) is shown boxed.

TABLE 5

| Primer Name | | Sequence |
|---|---|---|
| Ex19_M_F | SEQ ID NO: 6 | 5'TAAAATTCCCGTCGCTATCAA3' |
| Ex19_M_R | SEQ ID NO: 7 | 5'TGTGGAGATGAGCAGGGTCTAG3' |
| Ex19_WT_F | SEQ ID NO: 8 | 5'CTGTCAGTTAAGAGAAGCAACATCTCC3' |
| Ex19_WT_R | SEQ ID NO: 9 | 5'AGAGCAGCTGCCAGACATGAG3' |

Figure 11:
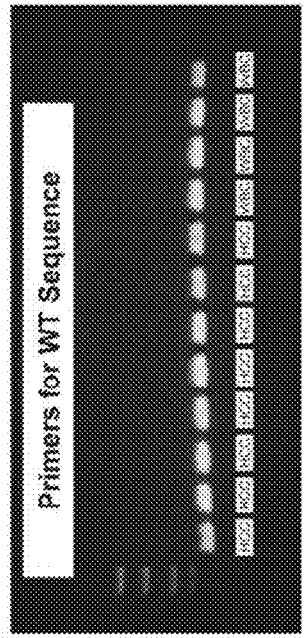
FIG. 11 shows an image of a gel electrophoresis of the separated products of a PCR amplification of M and WT individual cells performed with the mutated primer pair of Example 5.
Figure 12:
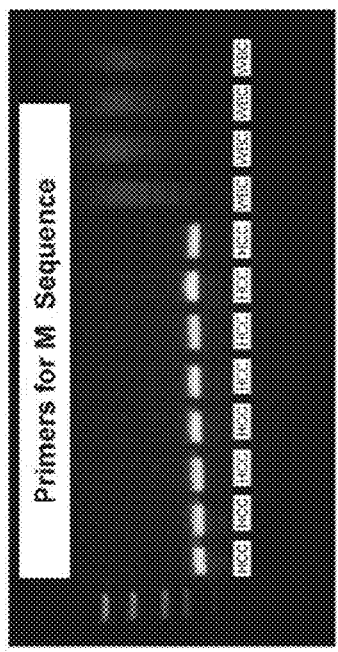
FIG. 12 shows an image of a gel electrophoresis of the separated products of a PCR amplification of M and WT individual cells performed with the wild-type primer pair of Example 5.

FIG. 11 shows the results of PCR amplification of M and WT individual cells with M primer pairs, while Figure shows the results of PCR amplification of M and WT individual cells with WT primer pairs.

Figure 13:
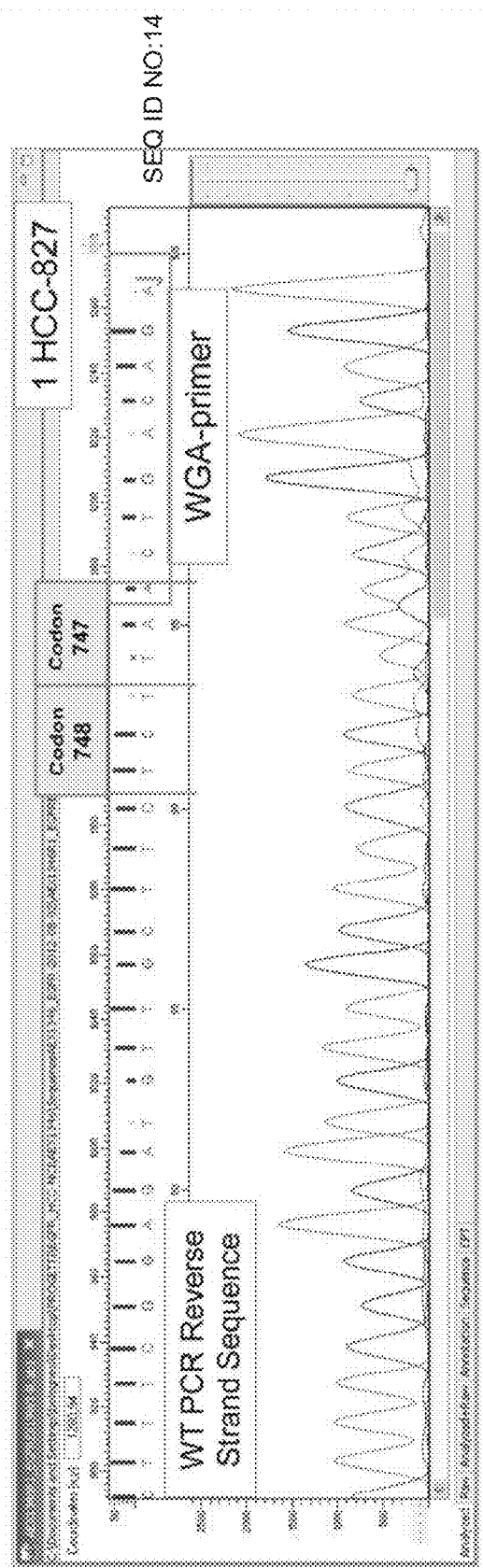
FIG. 13 shows an example of reverse strand sequence of a wild-type single cell of example 6.
Figure 14:
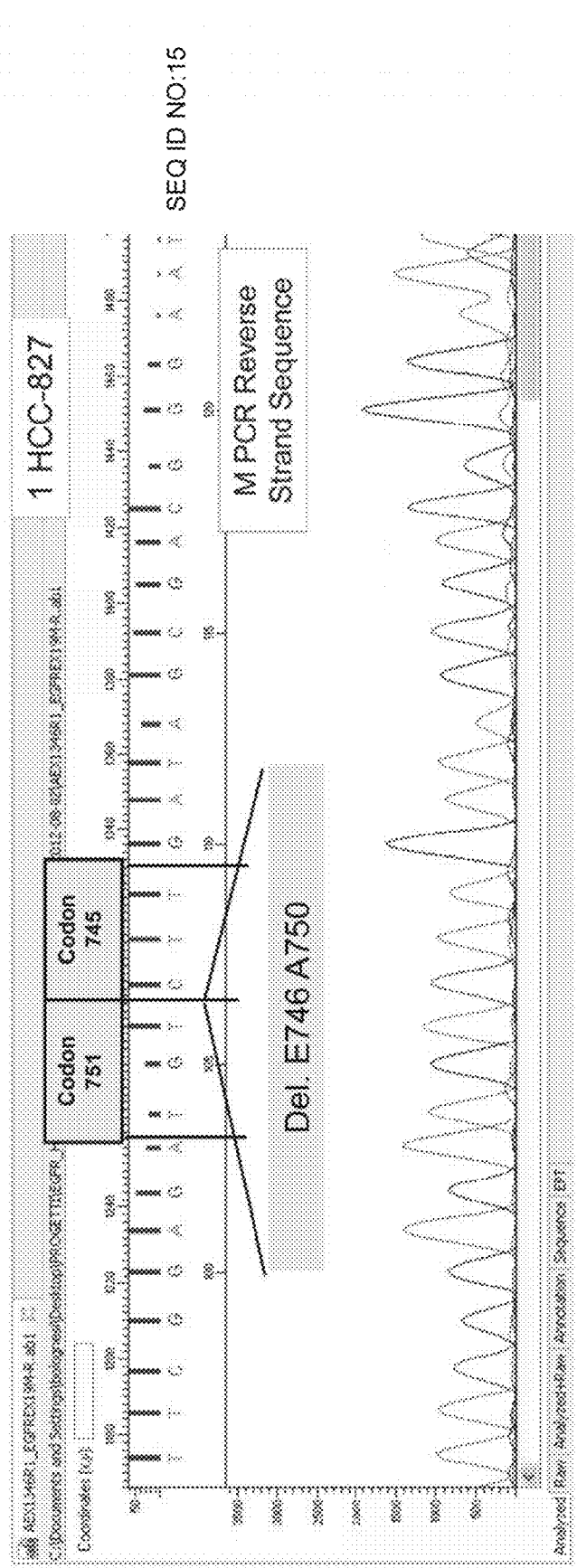
FIG. 14 shows an example of reverse strand sequence of a mutated single cell of example 6.

FIG. 13 shows a reverse strand sequence of a WT single cell, compared to the gDNA amplified with DRS-WGA, while FIG. 14 shows a reverse strand sequence of a M single cell, compared to the gDNA amplified with DRS-WGA.

Example 6

Removal of a RS in the Mutant Allele (EGFR Gene)—Assay Validation

The method described above has been further validated with 60 single cells:
  31 single HCC-827, treated according Veridex CellSearch enrichment protocol;
  11 single lymphocytes, treated according Veridex Cell-Search enrichment protocol;
  17 single fresh, live lymphocytes.

The method amplified the WT allele in 28/31=90% of the single HCC-827 and the M allele in 31/31=100% of the single HCC-827.

Considering the 11 Veridex-treated lymphocytes, 11/11=100% resulted in a positive PCR product for the WT PCR, 3/11=27% resulted in a positive PCR product for the M-PCR. These products were sequenced and confirmed to be WT. Hence, detecting the DNA by sequencing, the specificity on Veridex-treated lymphocytes is still 100%, whereas, just relying on the PCR positivity the specificity is (in this test) 8/11=73%. Detecting the DNA product length by gel electrophoresis would similarly allow to distinguish the length and determine that actually it is WT; detecting the DNA product by real-time PCR would not distinguish between WT and M products. Considering the 17 fresh lymphocytes, 17/17=100% resulted in a positive PCR product for the WT PCR, 0/17=0% resulted in a positive PCR product for the M-PCR. These products were sequenced and confirmed to be WT.

As there are 2 WT alleles per lymphocyte, the difference in undigested RS between Veridex-treated (3/22=14%) and fresh lymphocytes (0/34=0%) is statistically significant.

This demonstrates the robustness of the above described method in case of incomplete RE digestion activity.

Results are shown in FIG. 15 and summarised in Table 6.

TABLE 6

| | | | EGFR Exon19 | |
|---|---|---|---|---|
| | Treatment | n | PCR of WT Allele | PCR of Del. E746_A750 M Allele |
| HCC-827 | Veridex | 31 | 90% | 100% |
| WBC | Veridex | 11 | 100% | 27% (*) |
| WBC | Fresh | 17 | 100% | 0% |

(*) All sequences WT

The above examples show that the method according to the present invention guarantees the amplification (and the sequencing) even in case of incomplete digestion activity of the restriction endonuclease. The activity of the RE cannot always guarantee the effective digestion of all the RS present in the target DNA, because of the treatment which the cells have been subjected to (as in the previous example), or for other reasons linked to the specific sequence around the restriction site.

Statistically a small percentage of undigested RS is present in the DRS-WGA, which nevertheless are successfully Whole Genome Amplified, albeit with the universal (primary—PCR) primer being connected to another RS.

In case of an undigested site the use of just one PCR for the third target sequence (with the MDRS) would not allow the amplification and the sequencing of said target. In case of incomplete DNA digestion by the restriction enzyme, the method of the invention allows the detection of both WT and M allele when they are present in the DRS-WGA library.

Figure 16:
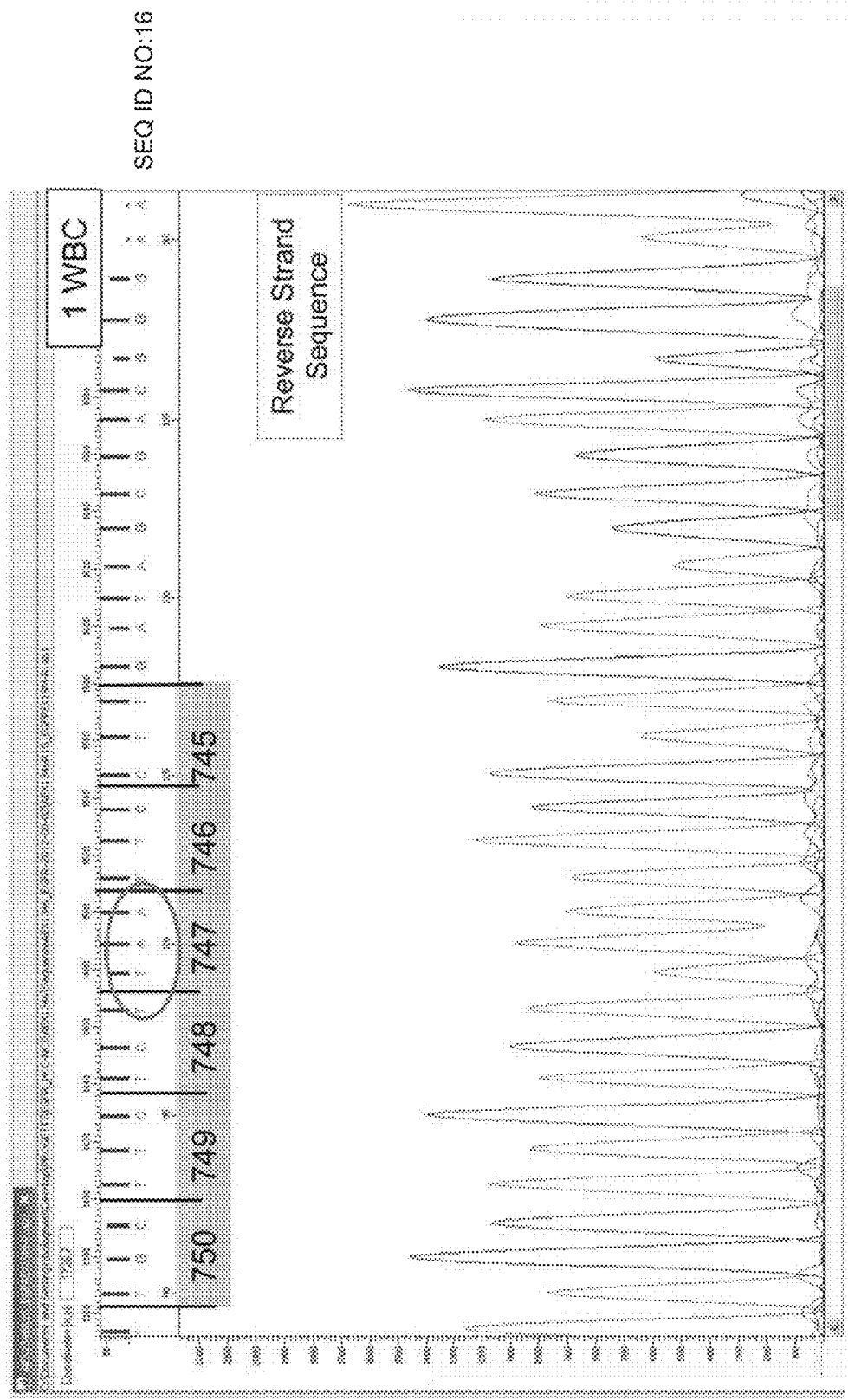
FIG. 16 shows an example of reverse strand sequence of a wild-type cell (a leukocyte) positive for mutant PCR product (i.e. a false positive for PCR product alone), which was instead confirmed to be wild-type by the assay as in Example 6.

FIG. 16 shows an example of the sequencing results of one of the three Veridex-treated lymphocytes positive for the M-PCR. This is the case of the second target sequence (with the MDRS, but undigested during WGA), being amplified and sequenced correctly with the second forward primer.

Example 7

Introduction of a New RS in the Mutant Allele (PIK3CA Gene)

As another example, mutation M1043I, of the exon 21 of the PIK3CA gene stemming from the single nucleotide change ATG/TAAT, can be detected by the method according to the present invention.

From an analysis of the features of the method and kit of the present invention, the resulting advantages are apparent.

In particular, in virtue of the particular design of the primers used to amplify by PCR the library of DNA sequences, the method allows to differentially detect the first target DNA sequence and the second target DNA sequence (differing in the presence of a restriction site for the restriction endonuclease of the DRS-WGA) with great specificity and robustness.

Further, the use of a fourth reverse primer allows an even more specific and robust detection and an amplicon-size based detection, which is fast, simple and cost-effective.

Further, the method of the present invention may be applied downstream of deterministic restriction site whole genome amplification to detect mutations in a specific and robust manner. These mutations are impossible to otherwise detect with the traditional detection methods available.

Moreover, the use of a DNA sequencing method, in particular Sanger sequencing or pyrosequencing, guarantees the correct detection of even the false positives which could occur in the case of incomplete digestion of the restriction endonuclease of the DNA library.

Furthermore, a percentage of identity from 20% to 80%, better from 40% to 60%, of the third forward primer with the WGA primer allows to obtain an optimal result.

Finally, it is clear that modifications and variants to the method and kit disclosed and shown may be made without because of this departing from the scope of protection of the appended claims.

In particular, the method may be multiplexed by using further pairs of primers which do not interfere with the PCR amplification with the first, second, third and possibly fourth primer.

Additionally, one or more of said primers may further include a 5' end sequence which does not hybridize to any of said first or second target sequence positive or antipositive strand. This feature can advantageously be used for one or more of the following purposes:
barcoding the PCR products with a sample tag,
introducing in the PCR product an adaptor for next-generation sequencing
preventing spurious priming in multiplexed target PCR reaction.

Furthermore, as the WGA products from the PCR reaction may display some background signal, it may be of advantage to use a different primer for sequencing. This adds an extra layer of specificity, improving the signal-to-noise and readability of the sequence plot.

The invention claimed is:

1. A method for detecting at least one of at least one first target DNA sequence and at least one second target DNA sequence from a library of DNA sequences, wherein the first target DNA sequence differs from the second target DNA sequence in that a single or multiple nucleotide substitution or deletion or insertion in the second target sequence generates a restriction site for a restriction endonuclease, giving rise—if cleaved by the restriction endonuclease—to a first cleaved second target sequence 3' of the generated restriction site and a second cleaved second target sequence 5' of the generated restriction site, comprising the steps of:
(a) providing the library of DNA sequences, each of the DNA sequences comprising, respectively from the 5' end to the 3' end, a first sequence segment having a length from 15 to 50 nucleotides, a second sequence segment of genomic DNA as cleaved by the restriction endonuclease, and a third sequence segment reverse complementary to the union of the first sequence segment and, if any, the 5' overhang generated by the restriction endonuclease;
(b) amplifying the library of DNA sequences by PCR using:
at least one first reverse primer which hybridises to the 3' end region of the second sequence segment of the at least one first target sequence positive strand or at least first cleaved second target sequence positive strand;
at least one second forward primer which hybridises to the 3' end region of the second sequence segment of the at least one first target sequence antipositive strand;
at least one third forward primer comprising a first 5' portion hybridising to the 5' end region of the third sequence segment of the at least first cleaved second target sequence antipositive strand and a second 3' portion hybridising to the 3' end region of the second sequence segment of the at least one first cleaved second target sequence antipositive strand, wherein the first portion of the at least one third forward primer has a length from 20% to 80% with respect to the total length of the at least one third forward primer;
(c) detecting DNA sequences amplified in step (b).

2. The method according to claim 1, wherein step (b) further uses at least one fourth reverse primer which hybridises to the 3' end region of the second sequence segment of the at least one second target sequence positive strand.

3. The method according to claim 1, wherein the library of DNA sequences is obtained by deterministic restriction site whole genome amplification.

4. The method according to claim 1, wherein step (c) is performed by a DNA sequencing method.

5. The method according to claim 4, wherein the DNA sequencing method is Sanger sequencing or sequencing by synthesis.

6. The method according to claim 1, wherein the first portion of the at least one third forward primer has a length from 40% to 60% with respect to the total length of the at least one third forward primer.

7. The method according to claim 1, wherein said second portion of the at least one third forward primer has a length in bases comprised between a minimum corresponding to the consensus sequence of said restriction endonuclease minus, if any, the 5' overhang generated by the restriction endonuclease, all divided by two, and a maximum of 30 bases.

8. The method according to claim 1, wherein at least one of said primers further comprises a 5' end region which does not hybridize to any of said first or second target sequence, positive or antipositive strand.

9. The method according to claim 1, wherein the restriction endonuclease is MseI.

10. A kit comprising a first, a second and a third primer according to claim 1.

11. The kit according to claim 10 for use in the diagnosis of ALK or EGFR or PIK3CA mutations.

* * * * *